United States Patent [19]

Sartorelli et al.

[11] Patent Number: 4,849,563
[45] Date of Patent: Jul. 18, 1989

[54] NOVEL 1-ALKYL-1-ARENESULFONYL-2-ALKOXYCARBONYLSULFENYLHYDRAZINES HAVING ANTINEOPLASTIC ACTIVITY

[75] Inventors: Alan C. Sartorelli, Woodbridge; Krishnamurthy Shyam, Hamden; Robert T. Hrubiec, Meriden, all of Conn.

[73] Assignee: Yale University, New Haven, Conn.

[21] Appl. No.: 142,354

[22] Filed: Dec. 28, 1987

Related U.S. Application Data

[63] Continuation of Ser. No. 820,114, Jan. 21, 1986, abandoned.

[51] Int. Cl.[4] .................. A61K 31/63; A61K 31/265; A61K 31/18; C07C 154/00
[52] U.S. Cl. .................... 514/155; 514/602; 514/603; 514/604; 514/562; 562/427; 562/430; 564/81; 560/10; 560/12
[58] Field of Search ............... 564/80, 81; 514/602, 514/603, 604, 908, 155, 562; 562/427, 430; 260/397.7 R

[56] References Cited

U.S. PATENT DOCUMENTS 4,218,465  8/1980  Grange et al. .................. 514/908 X
4,684,747  8/1987  Sartorelli et al. ..................... 564/81

OTHER PUBLICATIONS

Reed, "Procarbazine", Antineoplastic and Immunosuppressive Agents, Part & ed. by Sartorelli et al, 1975, pp. 747–765.
Friedman et al, Org. Synth. Coll. vol. 5, 1055 (1973).
Shyam et al, J. Med. Chem., 1985, 28, 527–7.
Vincent T. DeVita, Jr., "Principles of Chemotherapy", Chapter 13, Cancer Principles and Practice of Oncology.
G. P. Wheeler and S. Chumley, "Alkylating Activity of 1,3-Bis(2-chloroethyl)-1-nitrosourca and Related Compounds", J. Med. Chem., 10, 259 (1967).
K. Shyam, L. A. Cosby and A. C. Sartorelli, "Synthesis and Evaluation of N,N[1]-Bis(arylsulfonyl)hydrazines as Antineoplastic Agents", Am. Chem. Society 1985, pp. 525–427.
L. Friedman, R. L. Litle, and Walter R. Reichle, "p-Toluenesulfonylhydrazide*", Organic Syntheses, pp. 1055–1057 (1973).

Primary Examiner—Charles F. Warren
Assistant Examiner—Carolyn S. Greason
Attorney, Agent, or Firm—Ostrolenk, Faber, Gerb & Soffen

[57] ABSTRACT

Compounds of the formula:

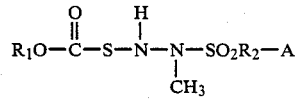

wherein $R_1$ is an alkyl of 1–6 carbon atoms, benzyl, phenyl, or phenyl substituted by halogen, alkoxy of 1 to 4 carbon atoms, alkyl of 1 to 4 carbon atoms, amino, or carbonyl substituents, or $-RN(R')_2$ wherein R and R' are each independently an alkyl of 1 to 4 carbon atoms; $R_2$ is an aromatic substituent selected from the group consisting of phenyl, benzyl, and naphthyl, and A is an aromatic substitution selected from the group consisting of hydrogen, alkyl of 1–4 carbon atoms, alkoxy of 1–4 carbon atoms, halogen, $-NO_2$, $-NH_2$, $-COOH$, and $-NHCOCH_3$. The compounds have been found to be alkylating agents having antineoplastic activity for use in inhibiting the growth of tumors.

20 Claims, No Drawings

NOVEL 1-ALKYL-1-ARENESULFONYL-2-ALKOXYCARBONYLSULFENYLHYDRAZINES HAVING ANTINEOPLASTIC ACTIVITY

This research was supported in part by a U.S. Public Health Service Grant (Grant No. CA-02817) from the National Cancer Institute.

This is a continuation of application Ser. No. 820,114 filed on Jan. 21, 1986 now abandoned.

BACKGROUND OF THE INVENTION

1. Field of the Invention

This invention relates to novel compounds having antineoplastic activity at least against B16 melanoma tumors, i.e. activity for inhibiting the growth of such malignant tumors. More specifically, it relates to compounds of the class 1-alkyl-1-arenesulfonyl-2-alkoxycarbonylsulfenylhydrazines and their use in inhibiting malignant tumors. These novel compounds constitute a new class of alkylating agents.

2. Prior Art and Other Information

Alkylating agents capable of methylation of biological molecules form a useful group of antineoplastic agents, with procarbazine, streptozotocin and dacarbazine being examples of clinically active agents of this type.

Assignee herein has also discovered another class of N,N'-bis(sulfonyl)hydrazines useful for inhibiting the growth of malignant B16 melanoma tumors tumors. These compounds are described in U.S. Ser. No. 06/683,852 filed on Dec. 20, 1984 and also in U.S. Ser. No. 06/810,644 filed on Dec. 18, 1985, which is a continuation-in-part of U.S. Ser. No. 06/683,852. See also Shyam et al, J. Med. Chem., 28, 525 (1985). The compounds described therein are of a different structure and particularly active against both L1210 leukemia and B16 melanoma; whereas the compounds of this invention have significant activity against mice bearing the B16 melanoma.

OBJECTS AND SUMMARY OF THE INVENTION

An object of this invention is to provide a new class of alkylating agents having antineoplastic activity against B16 melanoma.

A further object is to provide compositions containing such agents in a form suitable for administration to host organisms.

A still further object is to provide a method for preparing the novel alkylating agents.

A still further object is to provide novel compounds which have activity against malignant B16 melanoma tumors.

This invention relates to compounds of the formula:

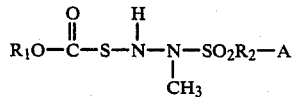

wherein $R_1$ is an alkyl of 1-6 carbon atoms, benzyl, phenyl, or phenyl substituted by halogen, alkoxy of 1 to 4 carbon atoms, alkyl of 1 to 4 carbon atoms, amino, or carbonyl substituents, or $-RN(R')_2$ wherein R and R' are each independently an alkyl of 1 to 4 carbon atoms, and $R_2$ is an aromatic substituent selected from the group consisting of phenyl, benzyl, and naphthyl, and A is an aromatic substitution selected from the group consisting of hydrogen, alkyl of 1-4 carbon atoms, alkoxy of 1-4 carbon atoms, halogen, $-NO_2$, $-NH_2$, $-COOH$, and $-NHCOCH_3$. The compounds have been found to be alkylating agents having antineoplastic activity for use in inhibiting the growth of at least malignant melanoma tumors, i.e. exhibit pronounced anti-tumor activity. In addition, they probably have low mammalian toxicity. The compounds may suitably be administered to a host organism internally in the form of conventional pharmaceutical preparations, for example, in conventional pharmaceutically acceptable enteral or parenteral excipients. These compounds are particularly active against B16 melanoma.

DETAILED DESCRIPTION OF THE INVENTION

The compounds described above are a new class of antineoplastic agents. A number of them have been synthesized and tested with demonstrable effectiveness against the B16 melanoma transplanted rodent tumors. These compounds possess the capacity to generate an alkylating species under physiological conditions. As indicated above, the compounds have the general formula:

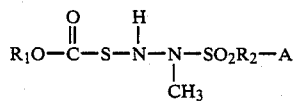

$R_1$ is an alkyl of 1-6 carbon atoms. As used herein, the term "alkyl" represents straight or branched chain carbon atoms. Preferably, $R_1$ is methyl, but may also be ethyl, isopropyl, or tert-butyl.

$R_1$ may also be a benzyl or a phenyl substituent or a phenyl substituent substituted by halogen, alkoxy of 1 to 4 carbon atoms, alkyl of 1 to 4 carbon atoms, amino or carbonyl substituents.

$R_1$ may also be $-RN(R')_2$ wherein R and R' may each independently be an alkyl of 1 to 4 carbon atoms, e.g. R' is $-CH_2CH_2$ and R' is $CH_3$.

$R_2$ is an aromatic substituent selected from the group consisting of:

phenyl: 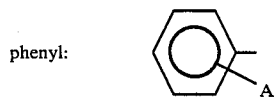

benzyl: 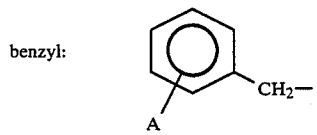

1 or 2 naphthyl: 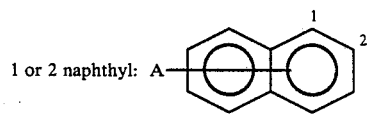

The preferred compounds are phenyl and benzyl.

A is an aromatic substitution which may be hydrogen. When this occurs, the phenyl, benzyl and naphthyl substituents are considered unsubstituted. Otherwise, the phenyl, benzyl and naphthyl substituents may be substituted by an A which is an alkyl of 1–4 carbon atoms, including straight or branched chain hydrocarbons, an alkoxy of 1–4 carbon atoms or halogen. The term "halogen" is meant to include all four halogens, namely chlorine, bromine, iodine and fluorine. Chlorine and bromine are the preferred halogens. Additionally, the phenyl, benzyl and naphthyl substituents may be substituted by a —NO$_2$, —NH$_2$, —COOH, or —NHCOCH$_3$ substituent.

The compounds of this invention may be made by the methodology shown in Scheme I:

SCHEME I

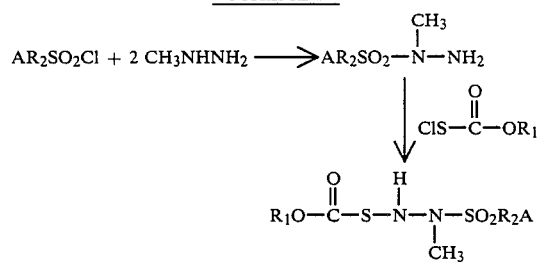

wherein R$_1$, R$_2$ and A are as previously defined.

The N-methyl-N-arenesulfonylhydrazides were prepared by reacting the appropriate arenesulfonyl chloride with methylhydrazine in a 1:2 molar ratio in tetrahydrofuran, see Friedman, et al, Org. Synth. Coll. Vol. 5, 1055 (1973), the entire disclosure of which is incorporated herein by reference. The appropriate arenesulfonyl chloride may be obtained commercially. The action of these intermediates in diethyl ether with about one equivalent of pyridine and one equivalent of alkoxycarbonylsulfenyl chloride produce the claimed products herein. Other solvents may be used, e.g. methylene chloride, chloroform. Furthermore, other organic bases may also be incorporated, e.g. triethylamine, lutidine.

The compounds of this invention are preferably administered internally, in the form of conventional pharmaceutical preparations, for example, in conventional enteral or parenteral pharmaceutically acceptable excipients containing organic and/or inorganic inert carriers, such as water, gelatin, lactose, dimethylacetamide, starch, magnesium stearate, talc, plant oils, gums, alcohol, vaseline or the like. The pharmaceutical preparations can be in solid forms, for example, tablets, dragees, suppositories, capsules, or the like or conventional liquid forms, such as suspensions, emulsions or the like. If desired, they can be sterilized and/or contain conventional pharmaceutical adjuvants, such as preservatives, stabilizing agents, wetting agents, emulsifying agents, buffers, or salts used for the adjustment of osmotic pressure. The pharmaceutical preparations may also contain other therapeutically active materials.

The pharmaceutical preparation should include an amount of a compound of this invention effective for antineoplastic activity against B16 melanoma. The effective dosage will depend on the antineoplastic activity and toxicity of the particular compound employed, and is thus within the ordinary skill of the art to determine for any particular host mammal or other host organism. Suitable may be, for example, in the range of about 2–15 mg/kg for man.

Typical compounds of the present invention include:

(1) 1-Benzenesulfonyl-2-methoxycarbonylsulfenyl-1-methylhydrazine
(2) 2-Methoxycarbonylsulfenyl-1-methyl-1-(4-methylbenzenesulfonyl)hydrazine
(3) 1-(4-Methoxybenzenesulfonyl)-2-methoxycarbonylsulfenyl-1-methylhydrazine
(4) 1-(4-Bromobenzenesulfonyl)-2-methoxycarbonylsulfenyl-1-methylhydrazine
(5) 2-Methoxycarbonylsulfenyl-1-methyl-1-(α-toluenesulfonyl)hydrazine
(6) 2-Methoxycarbonylsulfenyl-1-methyl-1-(2-naphthalenesulfonyl)hydrazine
(7) 1-(4-Chlorobenzenesulfonyl)-2-methoxycarbonylsulfenyl-1-methylhydrazine
(8) 2-Methoxycarbonylsulfenyl-1-methyl-1-(4-nitrobenzenesulfonyl)hydrazine
(9) 1-(4-Acetamidobenzenesulfonyl)-2-methoxycarbonylsulfenyl-1-methylhydrazine The following is a theoretical mechanism by which the compounds of this invention are activated based on the examples shown herein and previous work. As previously demonstrated, a variety of 1-methyl-1,2-bis-(arenesulfonyl)hydrazines (see U.S. Ser. No. 06/683,852 filed on Dec. 20, 1984 and the continuation-in-part thereof U.S. Ser. No. 06/810,644, filed Dec. 18, 1985 and Shyam, Cosby and Sartorelli, J. Med. Chem., 28, 525 (1985)) have been shown to be effective against the L1210 leukemia and B16 melanoma in mice. These compounds have the following formula:

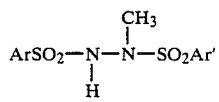
II

Ar and Ar' are aromatic substituents.

The compounds break down under physiological conditions to generate the putative alkylating species which has the formula:

III

This was hypothesized to account for the observed biological activity of these compounds.

Replacement of the 2-arenesulfonyl group in the compound of Formula II by a methoxycarbonylsulfenyl moiety to form a 1-methyl-1-arenesulfonyl-2-alkoxycarbonylsulfenylhydrazine of the following formula:

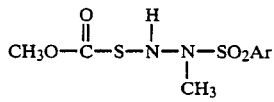
IV provided a compound which was capable of decomposing by the same mechanismm as the compounds of Formula II to give the methylating species shown below:

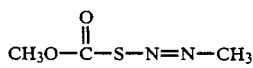
V

The compounds claimed herein also possess the ability to react directly with the sulphur atom of biological nucleophiles such as glutathione or various sulphur containing proteins to give methyldiazine, the postulated alkylating species derived from procarbazine (see Reed, "Procarbazine" in Antineoplastic and Immunosuppressive Agents, Part II ed. by Sartorelli and Johns. Berlin: Springer-Verlag, 1975, pp. 747–765) which can undergo further homolytic cleavage to generate the methyl radical, hydrogen radical and nitrogen. This is depicted in the Scheme II:

SCHEME II

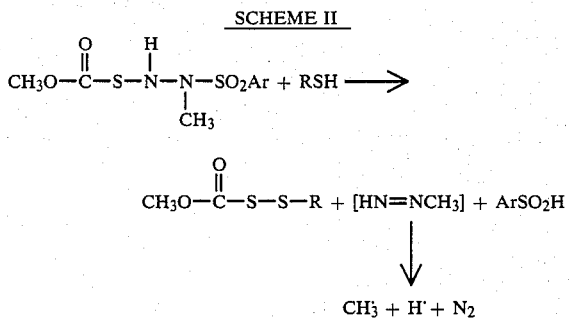

EXAMPLES OF COMPOUNDS

General procedure for the preparation of 1-methyl-1-arenesulfonyl-2-alkoxycarbonylsulfenylhydrazines.

Methoxycarbonylsulfenyl chloride (6.0 mmol) was slowly added dropwise to an ice-cold suspension of the appropriate 1-methyl-1-arenesulfonylhydrazide (6.0 mmol) (see the aforementioned Friedman et al) in anhydrous diethyl ether (50 ml) and pyridine (6.0 mmol) while maintaining the temperature below 10° C. After stirring at a temperature of between 0°–5° C. for 15 minutes, the mixture was filtered and the ethereal solution washed twice with ice-cold dilute hydrochloric acid (25 ml portions; 1:1, v/v) followed by three washings with brine (25 ml portions). The organic phase was dried (MgSO$_4$) and the diethyl ether evaporated in vacuo to give an oil which solidified upon trituration with light petroleum ether. Recrystallization from warm ethanol (50° C.) gave the pure compound. NMR spectral data were as expected.

TABLE I

Physical Constants for 1-Methyl-1-arenesulfonyl-2-methoxycarbonylsulfenylhydrazines.

| Compd | Ar(R$_2$-A) | Yield (%) | Mp.°C. | Formula |
|---|---|---|---|---|
| 1 | Phenyl | 82.7 | 62–63 (dec.) | $C_9H_{12}N_2O_4S_2$ |
| 2 | p-Tolyl | 73.7 | 92–93 (dec.) | $C_{10}H_{14}N_2O_4S_2$ |
| 3 | p-Methoxyphenyl | 76.2 | 74–75.5 (dec.) | $C_{10}H_{14}N_2O_5S_2$ |
| 4 | p-Bromophenyl | 78.6 | 98.5–100 (dec.) | $C_9H_{11}BrN_2O_4S_2$ |
| 5 | Benzyl | 41.3 | 82–84 (dec.) | $C_{10}H_{14}N_2O_4S_2$ |
| 6 | 2-Naphthyl | 84.7 | 91–92 (dec.) | $C_{13}H_{14}N_2O_4S_2$ |
| 7 | p-Chlorophenyl | 83.7 | 93.5–95 (dec.) | $C_9H_{11}ClN_2O_4S_2$ |
| 8 | p-Nitrophenyl | 44.0 | 133–134 (dec.) | $C_9H_{11}N_3O_6S_2$ |
| 9 | p-Acetamidophenyl | 36.4 | 100–102 (dec.) | $C_{11}H_{15}N_3O_5S_2$ |

Examples of B16 Melanoma Antitumor Activity

The B16 melanoma was propagated as a solid tumor in C57B1 mice. Transplanation was carried out by removing tumors from donor mice bearing 14-day subcutaneous tumor growths. The tissue was fragmented to make a well-dispersed cellular suspension and diluted with Fischer's medium without serum so that one gram of tissue was suspended in 5 ml of solution. A portion (0.2 ml) of the resulting cell suspension was injected intraperitoneally into each recipient animal. Dosage levels of all compounds were administered over a range of 12.5 to 50 mg/kg by intraperitoneal injection, beginning 24 hours after tumor implantation, once daily for 6 consecutive days. The test compounds were injected as fine suspensions following homogenization in 2 to 3 drops of 20% aqueous Tween 80 and then made up to volume with isotonic saline. All drugs were administered intraperitoneally in a volume of 0.5 ml and for experiments animals were distributed into groups of five mice of comparable weight and maintained throughout the course of the experiment on Laboratory Chow pellets and water ad libitum. Control tumor-bearing animals given injections of comparable volumes of vehicle were included in each experiment. Mice were weighed during the course of the experiments, and the percent change in body weight from onset to termination of therapy was used as an indication of drug toxicity. Determination of the sensitivity of neoplasms to these agents was based on the prolongation of survival time afforded by the drug treatments.

TABLE II

Effects of 1-Methyl-1-arenesulfonyl-2-methoxycarbonylsulfenylhydrazines on the Survival Time of Mice Bearing the B16 Melanoma

| Compd | Daily dose (mg/kg)$^a$ | Avg. Change in wt. (%)$^b$ | %T/C$^{c,d}$ | |
|---|---|---|---|---|
| 1 | 12.5 | −5.2 | 169 | |
|  | 25.0 | −13.0 | 183 | |
|  | 50.0 | −33.4 | 49 | |
| 2 | 12.5 | +0.7 | 182 | |
|  | 25.0 | −3.3 | 199 | |
|  | 50.0 | −17.7 | 232 | |
| 3 | 12.5 | −0.2 | 148 | |
|  | 25.0 | −6.4 | 160 | |
|  | 50.0 | −18.7 | 177 | |
| 4 | 12.5 | −2.0 | 144 | |
|  | 25.0 | −5.5 | 146 | |
|  | 50.0 | −11.4 | 160 | |
| 5 | 12.5 | −2.5 | 152 | |
|  | 25.0 | −14.8 | 157 | |
|  | 50.0 | −27.4 | 59 | |
| 6 | 12.5 | −0.2 | 123 | |
|  | 25.0 | +1.4 | 140 | |
|  | 50.0 | −4.8 | 163 | |
| 7 | 12.5 | −2.7 | 178 | |
|  | 25.0 | −2.5 | 187 | |
|  | 50.0 | −6.9 | 173 | |
| 8 | 12.5 | +0.5 | 176 | |
|  | 25.0 | +10.6 | 164 | |
|  | 50.0 | −1.0 | 173 | |
| 9 | 12.5 | +0.9 | 191 | |
|  | 25.0 | −1.7 | 222 | |
|  | 50.0 | +4.6 | 214 | |
| C$^e$ | 12.5 | +1.6 | 100 | (Comparative |
|  | 25.0 | +3.7 | 113 | Example) |
|  | 50.0 | −0.4 | 98 | |

$^a$Administered once daily for six consecutive days, beginning 24 hours after tumor transplantation, with 5 animals being used per group.
$^b$Average change in body weight from onset to termination of therapy.
$^c$% T/C = average survival time of treated/control animals × 100.
$^d$Each value represents the average of two experiments of 5 mice/group
$^e$Results from one experiment.

Compound "C" is 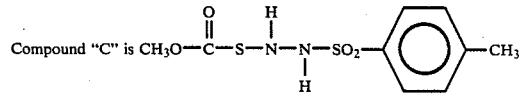

TABLE III

Effects of 1-Methyl-1-arenesulfonyl-2-methoxcarbonyl-sulfenylhydrazines on the Survival Time of Mice Bearing the L1210 Leukemia

| Compd | Daily dose (mg/kg)[a] | Avg. Change in wt. (%)[b] | % T/C[c,d] |
|---|---|---|---|
| 1 | 12.5 | +8.1 | 104 |
|   | 25.0 | +1.7 | 113 |
|   | 50.0 | −10.9 | 113 |
| 2 | 12.5 | +0.1 | 116 |
|   | 25.0 | +6.1 | 111 |
|   | 50.0 | −4.2 | 118 |
| 3 | 12.5 | +14.4 | 104 |
|   | 25.0 | +3.7 | 115 |
|   | 50.0 | −6.7 | 149 |
| 4 | 12.5 | +10.5 | 102 |
|   | 25.0 | +9.6 | 117 |
|   | 50.0 | −0.2 | 122 |
| 5 | 12.5 | +11.2 | 98 |
|   | 25.0 | +10.2 | 102 |
|   | 50.0 | −8.0 | 100 |

[a]Administered once daily for six consecutive days, beginning 24 hours after tumor transplantation, with 5 animals being used per group.
[b]Average change in body weight from onset to termination of therapy.
[c]% T/C = average survival time of treated/control animals × 100.
[d]Each value represents the average of two experiments of 5 mice/group.

Example of Determination of Alkylating Ability of Compounds

A solution of the test sample (12 micromol) in dimethylsulfoxide (1 ml), distilled water (2 ml), Tris-HCl buffer (pH 7.4; 1 ml) was incubated with 4-(4-nitrobenzyl)pyridine (148 micromol in 0.4 ml acetone) at 37° C. for 1 hour. Following addition of acetone (2 ml) and 0.25M sodium hydroxide solution (1.5 ml), the material was extracted with ethyl acetate (5 ml) and the absorbance determined at 540 nm.

TABLE IV

Comparison of the Degree of Alkylation of 4-(4-Nitrobenzyl) pyridine and Antineoplastic Activity of 1-Methyl-1-arenesulfonyl-2-methoxycarbonylsulfenylhydrazines.

| Cmpd | Alkylating Ability[a] (absorbance 540 nm) | Antineoplastic Activity (maximum % T/C from Table II) |
|---|---|---|
| C | 0.02 | 113 |
| 5 | 0.30 | 157 |
| 2 | 0.37 | 232 |
| 3 | 0.39 | 177 |
| 1 | 0.45 | 183 |
| 6 | 0.46 | 163 |
| 4 | 0.55 | 160 |

[a]The greater the absorbance value, the greater the degree of alkylation.

Discussion of Results of Examples

The tumor-inhibitory properties of compounds 1–9 were determined by measuring their effects on the survival time of mice bearing the B16 melanoma. The results of tests conducted are summarized in Table II. All of the compounds synthesized displayed significant activity against the B16 melanoma, with increases in the survival time of tumor-bearing animals being between 40% and 132%. Although compounds 2 and 9 were somewhat more active than the other derivatives, no clear-cut correlation was evident between the leaving group ability of the arenesulfonyl substitution, i.e. —$SO_2R_2$—A, and antineoplastic activity in this system. The only difference between these compounds resided in the variation of the proposed leaving group and this did not appear to significantly alter their activity.

Compounds 1–5 were also evaluated for anti-cancer activity against mice bearing the L1210 leukemia and the results are summarized in Table III. All of these compounds were found to be inactive against this tumor with the exception of compound 3 which displayed only limited activity. This finding contrasts with previous results with 1-methyl-1,2-bis(arenesulfonyl)hydrazines which showed significant activity against the L1210 leukemia (see U.S. Ser. No. 06/683,852 filed on Dec. 20, 1985 and the continuation-in-part thereof, U.S. Ser. No. 06/810,644 filed Dec. 18, 1985, as well as Shyam et al, J. Med. Chem., 28, 525 (1985)). This suggests that these compounds decompose in vivo to form a different reactive species than that proposed for the 1-methyl-1,2-bis(arenesulfonyl)hydrazines, and that the 1-methyl-1-arenesulfonyl-2-alkoxycarbonylsulfenylhydrazines represent a different class of compounds with potential clinical activity.

A modification of the method of Wheeler and Chumley (J. Med. Chem., 10, 259 (1967)) was used to examine whether compounds 1–6 possessed alkylating ability. This method measured the absorbance at 540 nm of the alkylated product of 4-(4-nitrobenzyl)pyridine. The results of this assay are listed in Table IV. As expected, all of the compounds demonstrating antitumor activity against the B16 melanoma showed significant alkylating ability under the conditions employed. Furthermore, compound C, which may not generate a reactive methylating species, showed essentially no alkylating activity in this assay and was inactive against the B16 melanoma.

The data in Table IV support the hypothetical mechanism described herein but the capacity to generate a reactive intermediate by direct attack of a nucleophile, as depicted herein, cannot be ruled out. It seems likely that the facility of these compounds to act as antineoplastic agents against B16 melanoma involves complex kinetics since two modes of activation are possible and may compete with each other. Furthermore, one cannot rule out the importance of pharmacodynamic mechanisms in the antitumor measurements.

Although the invention has been specifically described with reference to particular embodiments, it is to be understood that the invention is not limited to the particulars disclosed and extends to all equivalents within the scope of the claims.

What is claimed is:

1. A compound of the formula:

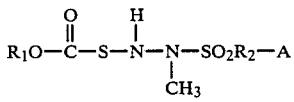

wherein
R₁ is methyl or ethyl;
R₂ is an aromatic substituent selected from the group consisting of phenyl, benzyl, and naphthyl; and
A is an aromatic substitution selected from the group consisting of hydrogen, alkyl of 1–4 carbon atoms, alkoxy of 1–4 carbon atoms, halogen, —$NO_2$, —$NH_2$, —COOH and —$NHCOCH_3$.

2. The compound of claim 1, wherein $R_1$ is methyl.
3. The compound of claim 1, wherein $R_1$ is ethyl.
4. The compound of claim 2, wherein $R_2$ is phenyl.
5. The compound of claim 2, wherein $R_2$ is benzyl.
6. The compound of claim 2, wherein $R_2$ is 2-naphthyl.
7. The compound of claim 4, wherein A is alkyl of 1–4 carbon atoms.

8. The compound of claim 4, wherein A is alkoxy of 1-4 carbon atoms.

9. The compound of claim 4, wherein A is halogen.

10. The compound of claim 1, wherein $R_1$ is methyl, $R_2$ is phenyl, and A is hydrogen.

11. The compound of claim 1, wherein $R_1$ is methyl, $R_2$ is phenyl, and A is methyl.

12. The compound of claim 1, wherein $R_1$ is methyl, $R_2$ is phenyl, and A is methoxy.

13. The compound of claim 1, wherein $R_1$ is methyl, $R_2$ is phenyl, and A is bromine.

14. The compound of claim 1, wherein $R_1$ is methyl, $R_2$ is benzyl, and A is hydrogen.

15. The compound of claim 1, wherein $R_1$ is methyl, $R_2$ is naphthyl, and A is hydrogen.

16. 2-Methoxycarbonylsulfenyl-1-methyl-1-(4-methylbenzenesulfonyl)hydrazine.

17. 1-(4-Acetamidobenezenesulfonyl)-2-methoxycarbonylsulfenyl-1-methylhydrazine.

18. An antineoplastic composition for B16 melanoma comprising an antineoplastically effective amount of a compound of claim 1 and a pharmaceutically acceptable carrier.

19. The composition of claim 18, where $R_1$ is methyl and A is selected from the group consisting of hydrogen, methyl, methoxy and bromine.

20. A method of inhibiting the growth of B16 melanoma tumors in host organisms which comprises administering to said host organism a B16 melanoma tumor inhibiting amount of the compound of claim 1.

* * * * *